(12) United States Patent
Logie et al.

(10) Patent No.: US 7,662,922 B2
(45) Date of Patent: Feb. 16, 2010

(54) CANOLA PROTEIN ISOLATE COMPOSITIONS

(75) Inventors: James Logie, Winnipeg (CA); Radka Milanova, Vancouver (CA)

(73) Assignee: Burcon Nutrascience (MB) Corp., Winnipeg, Manitoba (CA)

( * ) Notice: Subject to any disclaimer, the term of this patent is extended or adjusted under 35 U.S.C. 154(b) by 1027 days.

(21) Appl. No.: 10/413,371

(22) Filed: Apr. 15, 2003

(65) Prior Publication Data

US 2004/0034200 A1    Feb. 19, 2004

Related U.S. Application Data

(60) Provisional application No. 60/372,165, filed on Apr. 15, 2002, provisional application No. 60/430,687, filed on Dec. 4, 2002.

(51) Int. Cl.
| | |
|---|---|
| *A61K 36/00* | (2006.01) |
| *C08H 1/00* | (2006.01) |
| *A23J 1/00* | (2006.01) |
| *C07K 16/00* | (2006.01) |
| *C07K 1/00* | (2006.01) |
| *A61K 38/00* | (2006.01) |
| *A61K 51/00* | (2006.01) |

(52) U.S. Cl. .................. 530/376; 530/402; 530/412; 530/422; 530/427; 514/2; 424/1.69

(58) Field of Classification Search .......... 514/2
See application file for complete search history.

(56) References Cited

U.S. PATENT DOCUMENTS

| | | | |
|---|---|---|---|
| 4,370,267 A | 1/1983 | Lehnhardt et al. | |
| 5,844,086 A | 12/1998 | Murray | |
| 6,005,076 A | 12/1999 | Murray | |

FOREIGN PATENT DOCUMENTS

| | | | |
|---|---|---|---|
| JP | 0201611 | * | 8/1991 |
| JP | 5043597 A | | 2/1993 |

OTHER PUBLICATIONS

Vegetable Protein, Translated from French by V.G. Dolgopolov, Edited by T.P. Mikoulovich, Moscow VO "Agropromizdat", 1991, p. 150-153, 162-163.
Agropromyshlenny kompleks. L.A. Aksenova "RAPE" Mar. 7, 2001/found Oct. 8, 2007/ Internet:<http:// geo.1septemwer.ru/2001/07/3.htm.
Murray et al. "Rapeseed: a potential global source of high quality plant protein", (Apr. 2001), pp. 30-34 (Asia Pacific Food Industry, Apr. 2001).
XP-002246020 (Feb. 23, 1993), abstract.
Raab B. et al, Comparative study of the protein patterns of some rapeweed (*Brassica napus* L.) varieties by means of polyacrylamide gel electrophoresis and high-performance liquid chromatography: vol. 36, No. 3, pp. 239-247, 1992.
Krzyzaniak A. et al., The structure and properties of napin-seed storage protein from rap (*Brassica napus* L.), pp. 201-202, 1998.
James R. Witcox et al "Interrelationships among Seed Quality Attributes in Soybean" (Published in Corp. Sci. 41:11-14 (2001)).

* cited by examiner

*Primary Examiner*—Cecilia Tsang
*Assistant Examiner*—Maury Audet
(74) *Attorney, Agent, or Firm*—Michael I. Stewart; Sim & McBurney

(57) ABSTRACT

A new canola protein isolate is provided along with a new canola protein. The new canola protein isolate is obtained from the supernatant from the production of a canola protein micellar mass and contains a predominance of 2S protein, The canola protein isolate derived from PMM contains a predominance of a 7S protein. Compositions of the canola protein isolate are provided.

1 Claim, 7 Drawing Sheets

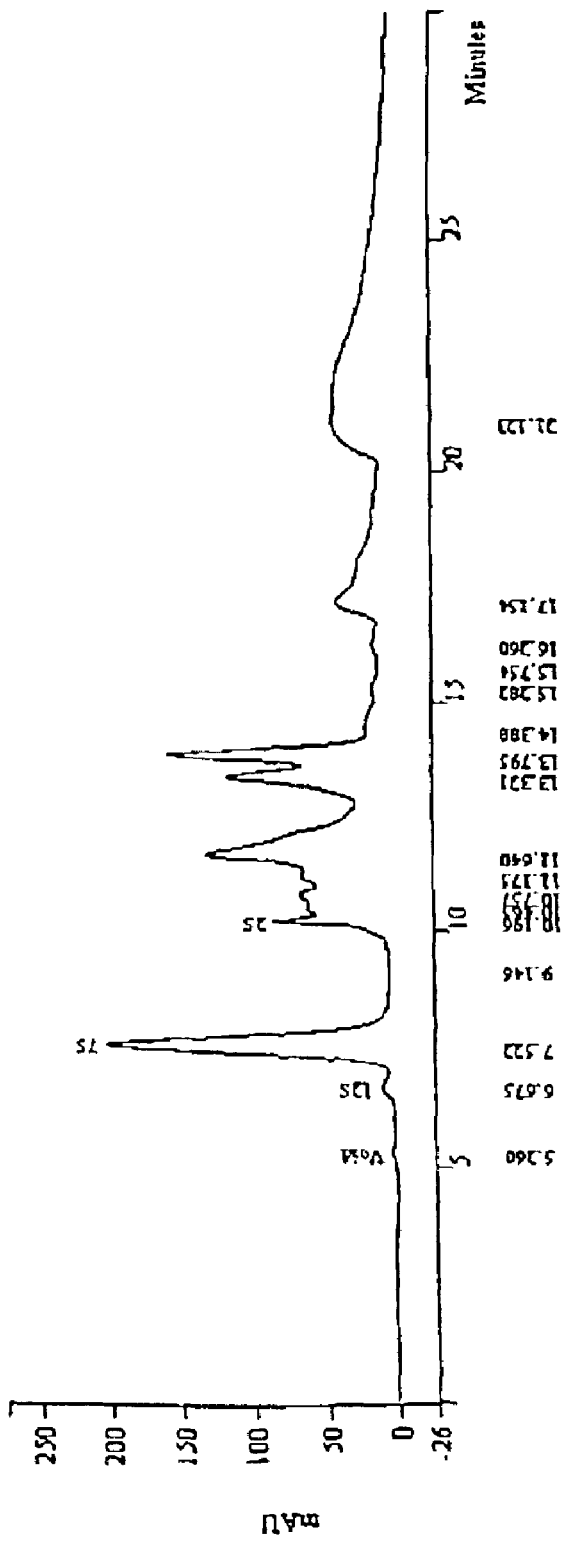
Figure 3 Analytical HPLC chromalogram of 0.05M saline extract of low temp meal at room temperature

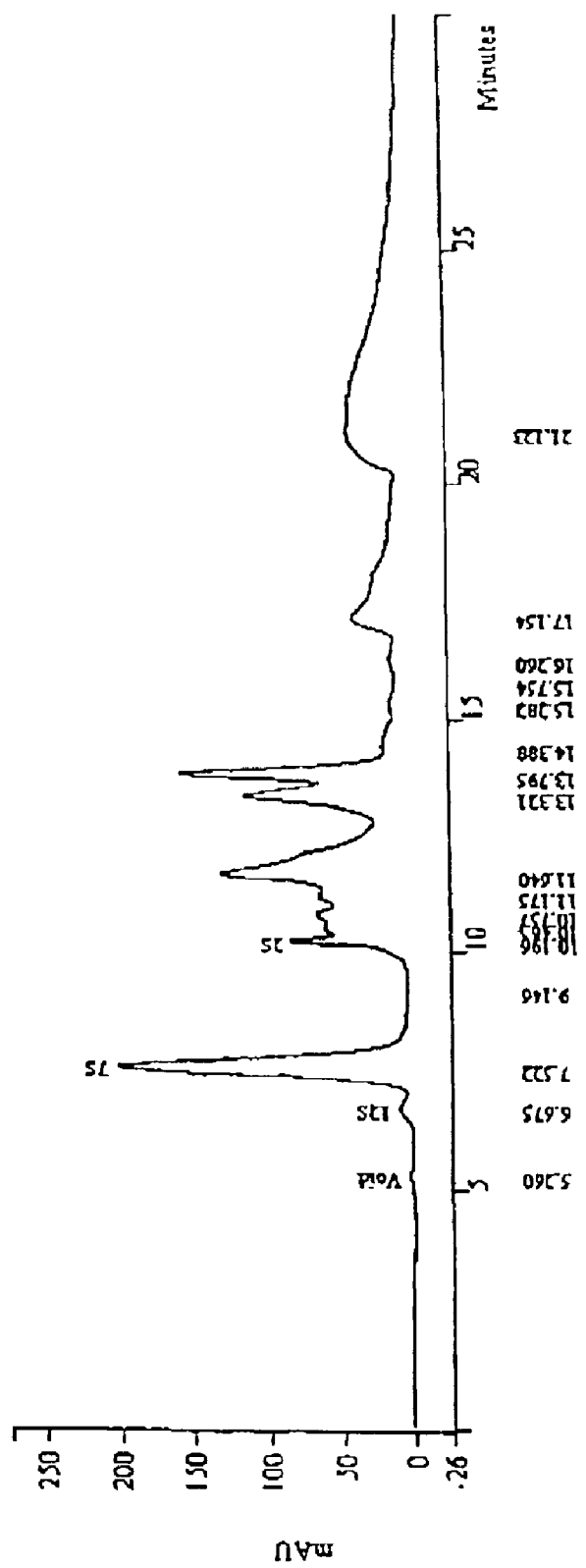
Figure 4 Analytical HPLC chromatogram of 0.10M saline extract of low temp meal at room temperature

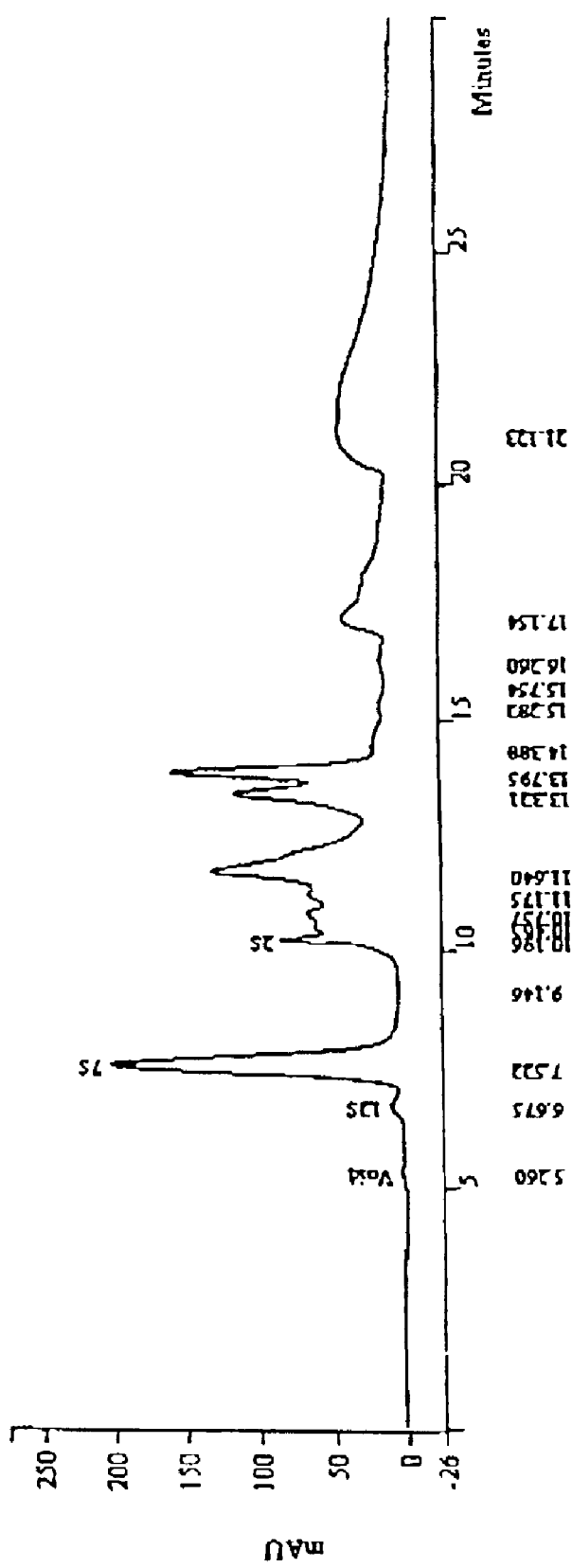
Figure 5 Analytical HPLC chromatogram of extract of low-temp meal at 60°C

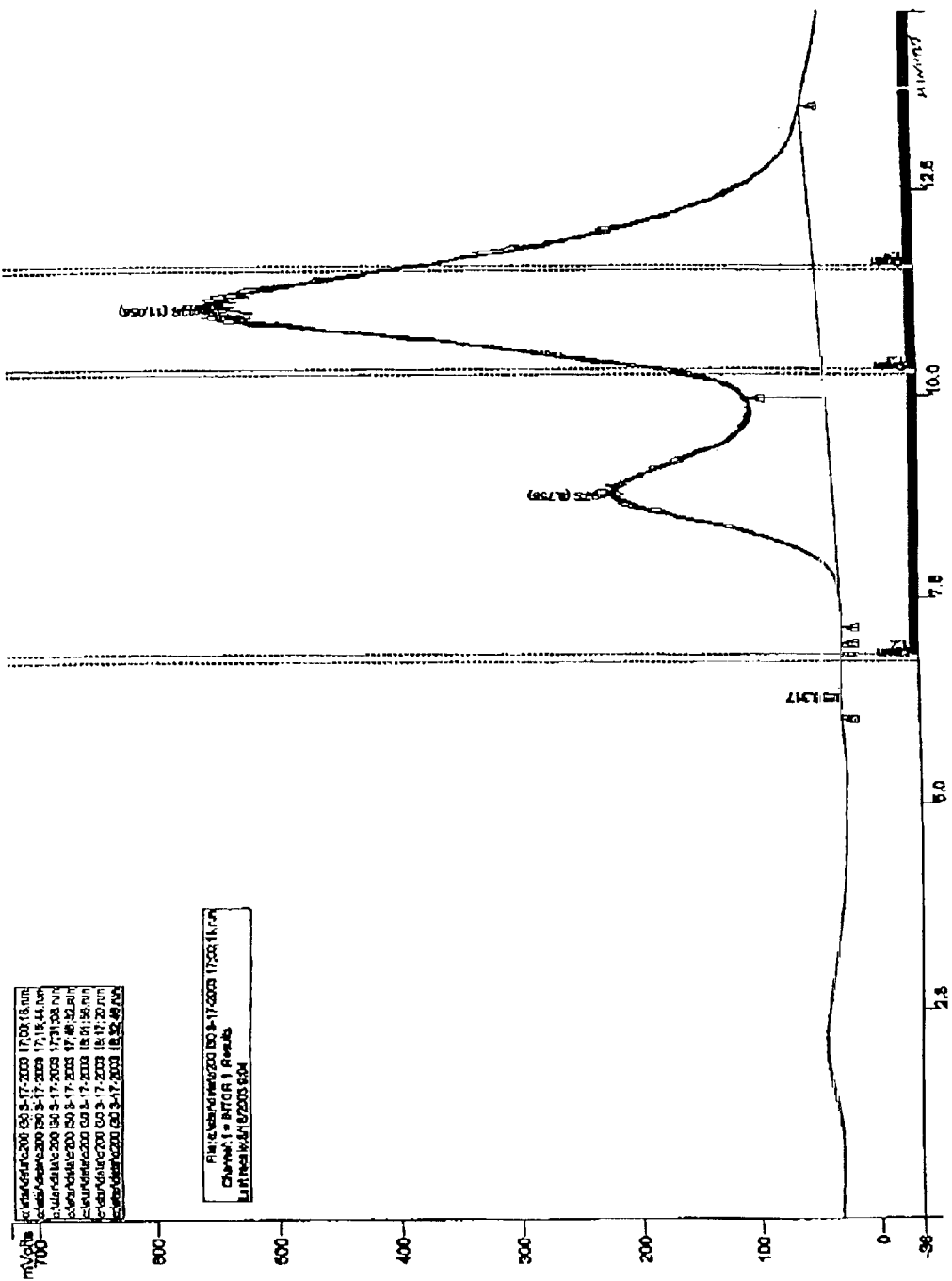
Figure 6. Overlay of 7 Consecutive Varian Prep-HPLC Runs of BW-AL021-I30-02A-C200 for 2S Fraction Collection on March 17, 2003. Run time: 15 minutes at 6 mL/min.

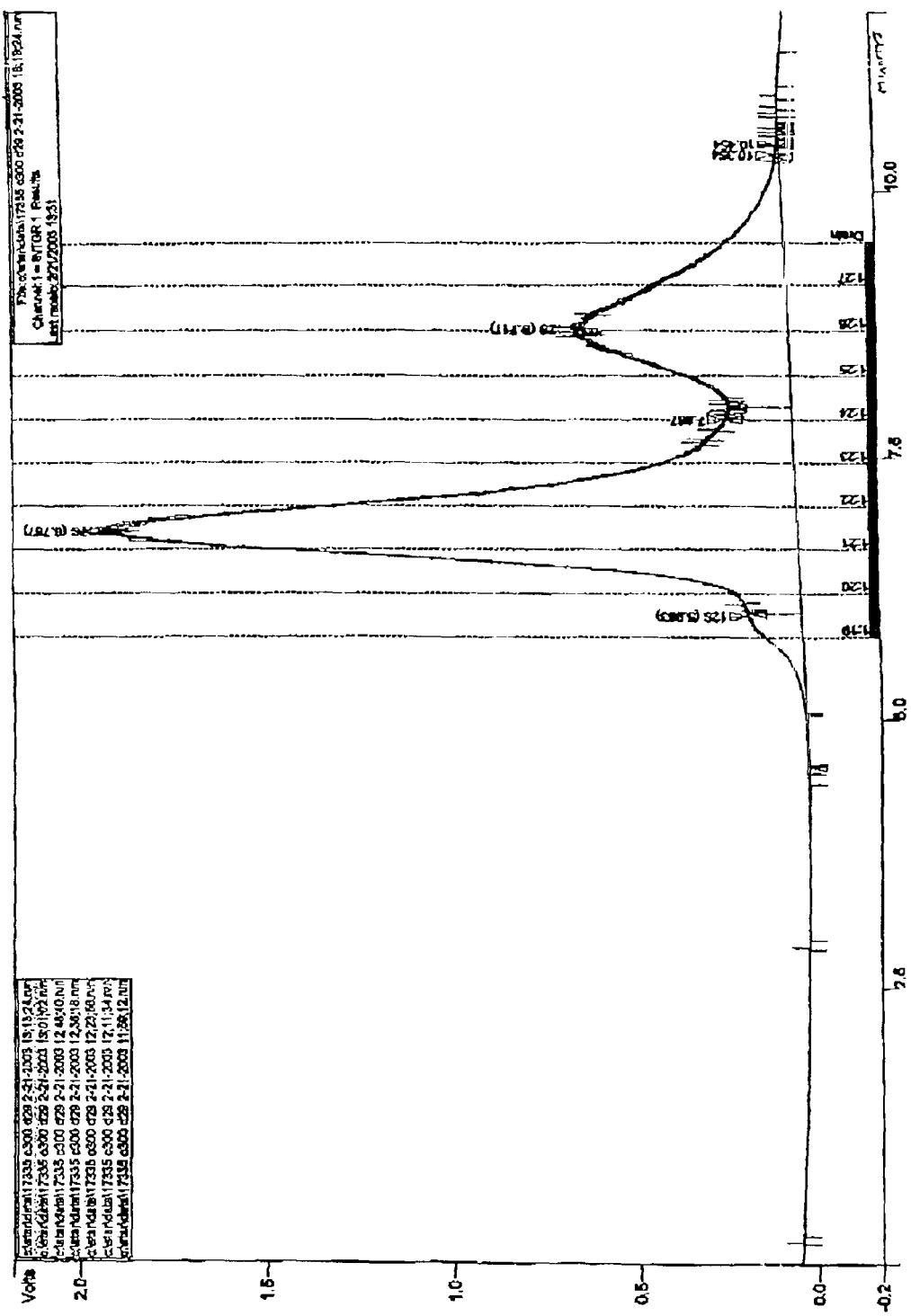
Figure 7. Overlay of 7 Consecutive Varian Prep-HPLC Runs of BW-AL017-D29-02A-C300 for 7S Fraction Collection on February 21, 2003. Run Time: 12 minutes @ 8 mL/min.

CANOLA PROTEIN ISOLATE COMPOSITIONS

REFERENCE TO RELATED APPLICATIONS

This application claims priority pursuant to 35 USC 119(e) from copending U.S. Patent Applications Nos. 60/372,165 filed Apr. 15, 2002 and 60/430,687 filed Dec. 4, 2002.

FIELD OF INVENTION

The present invention relates to canola protein isolate compositions and individual protein components of such compositions.

BACKGROUND TO THE INVENTION

Canola protein isolates can be formed from canola oil seed meal. In copending U.S. Patent Applications Nos. 60/288,415 filed May 4, 2001, 60/326,987 filed Oct. 5, 2001, 60/331,066 filed Nov. 7, 2001, 60/333,494 filed Nov. 26, 2001, 60/374,801 filed Apr. 24, 2002 and U.S. patent application Ser. No. 10/137,391 filed May 3, 2002 all assigned to the assignee hereof and the disclosures of which are incorporated herein by reference, there is described a method of making canola protein isolates from canola oil seed meal, such isolates having at least 100 wt % protein content (N×6.25). The procedure involves a multiple step process comprising extracting canola oil seed meal using a salt solution, separating the resulting aqueous protein solution from residual oil seed meal, increasing the protein concentration of the aqueous solution to at least about 200 g/L while maintaining the ionic strength substantially constant by using a selective membrane technique, diluting the resulting concentrated protein solution into chilled water to cause the formation of protein micelles, settling the protein micelles to form an amorphous, sticky, gelatinous gluten-like protein micellar mass (PMM), and recovering the protein micellar mass from supernatant having a protein content of at least about 100 wt % as determined by Kjeldahl nitrogen (N)×6.25. As used herein, protein content is determined on a dry weight basis. The recovered PMM may be dried.

In one embodiment of the process described above and as specifically described in Applications Nos. 60/326,987, 60/331,066, 60/333,494, 60/374,801 and application Ser. No. 10/137,391, the supernatant from the PMM settling step is processed to recover a protein isolate comprising dried protein from the wet PMM and supernatant. This procedure may be effected by initially concentrating the supernatant using ultrafiltration membranes, mixing the concentrated supernatant with the wet PMM and drying the mixture. The resulting canola protein isolate has a high purity of at least about 90 wt % of protein (N×6.25), preferably at least about 100 wt % protein (N×6.25).

In another embodiment of the process described above and as specifically described in Applications Nos. 60/333,494, 60/374,801 and application Ser. No. 10/137,391, the supernatant from the PMM settling step is processed to recover a protein from the supernatant. This procedure may be effected by initially concentrating the supernatant using ultrafiltration membranes and drying the concentrate. The resulting canola protein isolate has a high purity of at least about 90 wt % protein (N×6.25), preferably at least about 100 wt % protein (N×6.25).

The procedures described in the aforementioned US Patent Applications are essentially batch procedures. In copending U.S. Patent Applications Nos. 60/331,646 filed Nov. 20, 2001, 60/383,809 filed May 30, 2002 and U.S. patent application Ser. No. 10/298,678 filed Nov. 19, 2002, assigned to the assignee hereof and the disclosures of which are incorporated herein by reference, there is described a continuous process for making canola protein isolates. In accordance therewith, canola oil seed meal is continuously mixed with a salt solution, the mixture is conveyed through a pipe while extracting protein from the canola oil seed meal to form an aqueous protein solution, the aqueous protein solution is continuously separated from residual canola oil seed meal, the aqueous protein solution is continuously conveyed through a selective membrane operation to increase the protein content of the aqueous protein solution to at least about 200 g/L while maintaining the ionic strength substantially constant, the resulting concentrated protein solution is continuously mixed with chilled water to cause the formation of protein micelles, and the protein micelles are continuously permitted to settle while the supernatant is continuously overflowed until the desired amount of PMM has accumulated in the settling vessel. The PMM is removed from the settling vessel and may be dried. The PMM has a protein content of at least about 90 wt % as determined by Kjeldahl nitrogen (N)×6.25, preferably at least about 100 wt % (N×6.25).

As described in the aforementioned U.S. Patent Applications Nos. 60/326,987, 60/331,066, 60/333,494, 60/333,494, 60/374,801 and U.S. patent application Ser. No. 10/137,391, the overflowed supernatant may be processed to recover canola protein isolate therefrom.

Canola seed is known to contain about 10 to about 30 wt % proteins and several different protein components have been identified. These proteins are distinguished by different sedimentation coefficients (S). These known and identified proteins include a 12S globulin, known as cruciferin, and a 2S storage protein, known as napin.

Canola is also known as rapeseed or oil seed rape.

SUMMARY OF INVENTION

In addition to the 12S and 2S proteins, we have found that the procedures described above for the isolation of canola protein isolate produces significant quantities of a 7S protein, which appears to be a new protein. Accordingly, in one aspect of the invention, there is provided an isolated and purified 7S protein of canola.

We have also now found that the relative proportions of the 12S, 7S and 2S proteins differ as between protein micellar mass-derived canola protein isolate and supernatant-derived canola protein isolate, prepared using the above-described procedures. In particular, it has been found that PMM-derived canola protein isolate having a protein content of at least about 90 wt % N×6.25), preferably at least about 100 wt %, has a protein component content of about 60 to about 98 wt % of 7S protein, about 1 to about 15 wt % of 12S protein and 0 to about 25 wt % of 2S protein. By way of contrast, the supernatant-derived canola protein isolate having a protein content of at least about 90 wt % (N×6.25), preferably at least about 100 wt %, has a protein component content of 0 to about 5 wt % of 12S protein, about 5 to about 40 wt % of the 7S protein and about 60 to about 95 wt % of 2S protein.

The PMM-derived canola protein isolate preferably has a protein component content of about 88 to about 98 wt % of 7S protein, about 1 to about 10 wt % of 12S protein and 0 to about 6 wt % of 2S protein while the supernatant-derived canola protein isolate preferably has a protein component content of about 70 to about 95 wt % of 2S protein, about 5 to about 30 wt % of 7S protein and 0 to about 2 wt % of 12S protein.

The protein component profiles, therefore, are very different for the two canola protein isolates. In the case of the PMM-derived canola protein isolate the predominant protein species is the 7S protein while in the case of the supernatant-derived canola protein isolate, the predominant species is the 2S protein. These differences lead to different behaviour in environments where the canola protein isolates are employed.

The different protein content profiles enable canola protein isolate compositions to be provided wherein mixtures of the two different canola protein isolates are combined in any desired proportion for a specific application to provide any desired 2S/7S/12S protein profile as between that of the PMM-derived isolate and that of the supernatant-derived isolate.

The supernatant-derived isolate is a novel canola protein isolate. Accordingly, in another aspect of the present invention, there is provided a canola protein isolate having a protein content of at least about 90 wt %, preferably at least about 100 wt %, on a dry weight basis and at a Kjeldahl nitrogen conversion of N×6.25 and which exhibits a protein profile which is about 60 to about 95 wt % of 2S protein, about 5 to about 40 wt % of 7S protein and 0 to about 5 wt % of 12S protein. Preferably, the supernatant-derived canola protein isolate preferably exhibits a protein profile which is about 70 to about 95 wt % of 2S protein, about 5 to about 30 wt % of 7S protein and 0 to about 2 wt % of 12S protein.

The combination of the PMM-derived canola protein isolate product in any desired proportion with any desired proportion of the supernatant-derived canola protein isolate product to provide a composition containing desired proportions of 2S, 7S and 12S canola protein is a novel canola protein isolate composition. Accordingly, in another aspect, the present invention provides a canola protein isolate composition comprising (1) a first canola protein isolate having a protein content of at least about 90 wt %, preferably at least about 100 wt %, on a dry weight basis and at a Kjeldahl nitrogen conversion of N×6.25 and which exhibits a protein profile which is about 60 to about 98 wt % of 7S protein, about 1 to about 15 wt % of 12S protein and 0 to about 25 wt % of 2S protein, and (2) a second canola protein isolate leaving a protein content of at least about 90 wt %, preferably at least about 100 wt %, on a dry weight basis and a Kjeldahl nitrogen conversion of N×6.25 and which exhibits a protein profile which is about 60 to about 95 wt % of 2S protein, about 5 to about 40 wt %, of 7S protein and 0 to about 5 wt % of 12S protein.

The first canola protein isolate preferably exhibits a protein profile which is about 88 to about 98 wt % of 7S protein, about 1 to about 10 wt % of 12S protein and 0 to about 6 wt % of 2S protein. The second canola protein isolate preferably exhibits the preferred protein profile of the novel canola protein isolate described herein.

Variation in the proportions of the 12S/7S/2S proteins in a specific PMM-derived canola protein isolate and/or a specific supernatant-derived canola protein isolate may be achieved by varying the process conditions used to derive the respective canola protein isolates from canola oil seed meal.

The individual components of the canola protein isolate have been isolated, purified and characterized. The individual proteins may be separated from the respective PMM- and supernatant-derived canola protein isolates produced according to the procedures described above by any conventional procedure whereby protein mixtures may be separated based on size differences, preferably by preparative high pressure liquid chromatography (HPLC), followed by ultrafiltration to reduce the volume of eluant and dialysis to reduce residual solubilizing salt content. The dialyzed material may be dried to remove the pure protein.

The procedure for the isolating and purifying an individual canola proteins from a canola protein isolate containing a mixture of at least two different canola proteins selected from the group consisting of the 2S, 7S and 12S proteins, including the PMM-derived canola protein isolate and the supernatant-derived canola protein isolate described herein, constitutes a further aspect of the invention.

The 2S protein usually is isolated and purified from the supernatant-derived canola protein isolate while the 7S and 12S proteins usually are isolated and purified from the protein micellar mass. The 2S protein has a molecular weight, as determined by MALDI-MS, of about 14 kDa, the 7S protein has a molecular weight, as determined by MALDI-MS, of about 145 kDa and the 12S protein has a molecular weight, as determined by MALDI-MS, of about 290 kDa.

The 7S and 12S proteins have a very similar amino acid profile and are made up of numbers of the same subunits each containing approximately 413 amino acids. The 7S protein contains approximately 1240 amino acids while the 12S protein contains approximately 2480 amino acids. The 2S protein has a quite different amino acid profile from the 7S and 12S proteins and contains approximately 120 amino acids. The amino acid profiles obtained are set forth below in the Examples.

The provision of the individual isolated and purified 2S, 7S and 12S canola proteins enables there to be produced compositions of the 7S protein with different proportions of the 12S and/or 2S proteins in order to provide compositions which may have unique functionalities in the utilization of the purified proteins. Such compositions constitute another aspect of the present invention.

The canola protein isolates produced according to the process herein may be used in conventional applications of protein isolates, such as, protein fortification of processed foods, emulsification of oils, body formers in baked goods and foaming agents in products which entrap gases. In addition, the canola protein isolates may be formed into protein fibers, useful in meat analogs, may be used as an egg white substitute or extender in food products where egg white is used as a binder. The canola protein isolate may be used as nutritional supplements. Other uses of the canola protein isolate are in pet foods, animal feed and in industrial and cosmetic applications and in personal care products. The individual isolated and purified proteins may be put to similar use.

BRIEF DESCRIPTION OF DRAWINGS

FIGS. 3 to 5 are analytical HPLC chromatograms of extracts from low temperature meal; and FIGS. 6 and 7 contain overlap of seven consecutive preparative HPLC runs for the collection of individual 2S, 7S and 12S canola proteins.

GENERAL DESCRIPTION OF INVENTION

Figure 1:
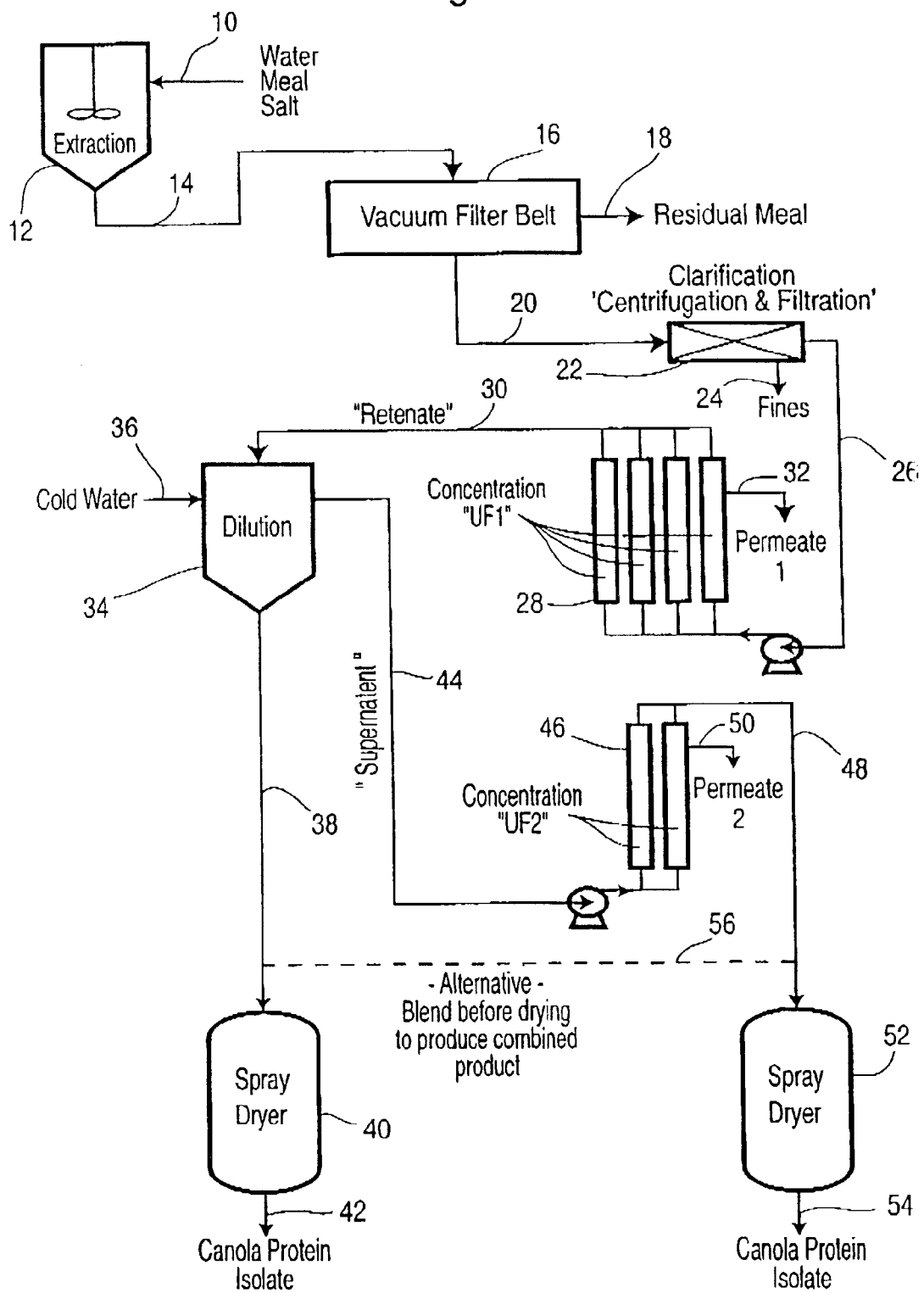
FIG. 1 is a schematic flow sheet of a procedure for producing canola protein isolates of differing protein profiles according to one embodiment of the invention.

The respective PMM-derived canola protein isolate and supernatant-derived canola protein isolate may be isolated from canola oil seed meal by either a batch process or a continuous process or a semi-continuous process as generally described in the aforementioned United States patent applications.

The initial step of the process of providing the canola protein isolates involves solubilizing proteinaceous material from canola oil seed meal. The proteinaceous material recovered from canola seed meal may be the protein naturally occurring in canola seed or other oil seed or the proteinaceous material may be a protein modified by genetic manipulation but possessing characteristic hydrophobic and polar properties of the natural protein. The canola meal may be any canola meal resulting from the removal of canola oil from canola oil seed with varying levels of non-denatured protein, resulting, for example, from hot hexane extraction or cold oil extrusion methods. The removal of canola oil from canola oil seed usually is effected as a separate operation from the protein isolate recovery procedure described herein.

Protein solubilization is effected most efficiently by using a food grade salt solution since the presence of the salt enhances the removal of soluble protein from the oil seed meal. Where the canola protein isolate is intended for non-food uses, non-food-grade chemicals may be used. The salt usually is sodium chloride, although other salts, such as, potassium chloride, may be used. The salt solution has an ionic strength of at least about 0.10, preferably at least about 0.15, to enable solubilization of significant quantities of protein to be effected. As the ionic strength of the salt solution increases the degree of solubilization of protein in the oil seed meal initially increases until a maximum value is achieved. Any subsequent increase in ionic strength does not increase the total protein solubilized. The ionic strength of the food grade salt solution which causes maximum protein solubilization varies depending on the salt concerned and the oil seed meal chosen.

In view of the greater degree of dilution required for protein precipitation with increasing ionic strengths, it is usually preferred to utilize an ionic strength value less than about 0.8, and more preferably a value of about 0.15 to about 0.6.

In a batch process, the salt solubilization of the protein is effected at a temperature of at least about 5° C. and preferably up to about 35° C., preferably accompanied by agitation to decrease the solubilization time, which is usually about 10 to about 60 minutes. It is preferred to effect the solubilization to extract substantially as much protein from the oil seed meal as is practicable, so as to provide an overall high product yield.

The lower temperature limit of about 5° C. is chosen since solubilization is impractically slow below this temperature while the upper preferred temperature limit of about 35° C. is chosen since the process becomes uneconomic at higher temperature levels in a batch mode.

In a continuous process, the extraction of the protein from the canola oil seed meal is carried out in any manner consistent with effecting a continuous extraction of protein from the canola oil seed meal. In one embodiment, the canola oil seed meal is continuously mixed with a food grade salt solution and the mixture is conveyed through a pipe or conduit having a length and at a flow rate for a residence time sufficient to effect the desired extraction in accordance with the parameters described herein. In such continuous procedure, the salt solubilization step is effected rapidly, in a time of up to about 10 minutes, preferably to effect solubilization to extract substantially as much protein from the canola oil seed meal as is practicable. The solubilization in the continuous procedure preferably is effect at elevated temperatures, preferably above about 35° C., generally up to about 65° C.

The aqueous food grade salt solution and the canola oil seed meal have a natural pH of about 5 to about 6.8 to enable a protein isolate to be formed by the micellar route, as described in more detail below.

At and close to the limits of the pH range, protein isolate formation occurs only partly through the micelle route and in lower yields than attainable elsewhere in the pH range. For these reasons, mildly acidic pH values of about 5.3 to about 6.2 are preferred.

The pH of the salt solution may be adjusted to any desired value within the range of about 5 to about 6.8 for use in the extraction step by the use of any convenient acid, usually hydrochloric acid, or alkali, usually sodium hydroxide, as required.

The concentration of oil seed meal in the food grade salt solution during the solubilization step may vary widely. Typical concentration values are about 5 to about 15% w/v.

The protein extraction step with the aqueous salt solution has the additional effect of solubilizing fats which may be present in the canola meal, which then results in the fats being present in the aqueous phase.

The protein solution resulting from the extraction step generally has a protein concentration of about 5 to about 40 g/L, preferably about 10 to about 30 g/L.

The aqueous phase resulting from the extraction step then may be separated from the residual canola meal, in any convenient manner, such as by employing vacuum filtration, followed by centrifugation and/or filtration to remove residual meal. The separated residual meal may be dried for disposal.

The colour of the final canola protein isolate can be improved in terms of light colour and less intense yellow by the mixing of powdered activated carbon or other pigment adsorbing agent with the separated aqueous protein solution and subsequently removing the adsorbent, conveniently by filtration, to provide a protein solution. Diafiltration also may be used for pigment removal.

Such pigment removal step may be carried out under any convenient conditions, generally at the ambient temperature of the separated aqueous protein solution, employing any suitable pigment adsorbing agent. For powdered activated carbon, an amount of about 0.025% to about 5% w/v. preferably about 0.05% to about 2% w/v, is employed.

Where the canola seed meal contains significant quantities of fat, as described in U.S. Pat. Nos. 5,844,086 and 6,005,076, assigned to the assignee hereof and the disclosures of which are incorporated herein by reference, then the defatting steps described therein may be effected on the separated aqueous protein solution and on the concentrated aqueous protein solution discussed below. When the colour improvement step is carried out, such step may be effected after the first defatting step.

As an alternative to extracting the oil seed meal with an aqueous salt solution, such extraction may be made using water alone, although the utilization of water alone tends to extract less protein from the oil seed meal than the aqueous salt solution. Where such alternative is employed, then the salt, in the concentrations discussed above, may be added to the protein solution after separation from the residual oil seed meal in order to maintain the protein in solution during the concentration step described below. When a colour removal step and/or a first fat removal step is carried out, the salt generally is added after completion of such operations.

Another alternative procedure is to extract the oil seed meal with the food grade salt solution at a relatively high pH value above about 6.8, generally up to about 9.9. The pH of the food grade salt solution, may be adjusted in pH to the desired alkaline value by the use of any convenient food-grade alkali, such as aqueous sodium hydroxide solution. Alternatively, the oil seed meal may be extracted with the salt solution at a relatively low pH below about pH 5, generally down to about pH 3. Where such alternative is employed, the aqueous phase resulting from the oil seed meal extraction step then is separated from the residual canola meal, in any convenient manner, such as by employing vacuum filtration, followed by centrifugation and/or filtration to remove residual meal. The separated residual meal may be dried for disposal.

The aqueous protein solution resulting from the high or low pH extraction step then is pH adjusted to the range of about 5 to about 6.8, preferably about 5.3 to about 6.2, as discussed above, prior to further processing as discussed below. Such pH adjustment may be effected using any convenient acid, such as hydrochloric acid, or alkali, such as sodium hydroxide, as appropriate.

The aqueous protein solution then is concentrated to increase the protein concentration thereof while maintaining the ionic strength thereof substantially constant. Such concentration generally is effected to provide a concentrated protein solution having a protein concentration of at least about 200 g/L, preferably at least about 250 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 3000 to about 50,000 daltons, having regard to differing membrane materials and configurations, and, for continuous operation, dimensioned to permit the desired degree of concentration as the aqueous protein solution passes through the membranes.

The concentration step may be effected at any convenient temperature, generally about 20° to about 60° C., and for the period of time to effect the desired degree of concentration. The temperature and other conditions used to some degree depend upon the membrane equipment used to effect the concentration and the desired protein concentration of the solution.

The concentrating of the protein solution to a concentration above about 200 g/L in this step not only increases the process yield to levels above about 40% in terms of the proportion of extracted protein which is recovered as dried protein isolate, preferably above about 80%, but also decreases the salt concentration of the final protein isolate after drying. The ability to control the salt concentration of the isolate is important in applications of the isolate where variations in salt concentrations affect the functional and sensory properties in a specific food application.

As is well known, ultrafiltration and similar selective membrane techniques permit low molecular weight species to pass therethrough while preventing higher molecular weight species from so doing. The low molecular weight species include not only the ionic species of the salt but also low molecular weight materials extracted from the source material, such as, carbohydrates, pigments and anti-nutritional factors, as well as any low molecular weight forms of the protein. The molecular weight cut-off of the membrane is usually chosen to ensure retention of a significant proportion of the protein in the solution, while permitting contaminants to pass through having regard to the different membrane materials and configurations.

Depending on the temperature employed in the concentration step, the concentrated protein solution may be warned to a temperature of at least about 20°, and up to about 60° C., preferably about 25° to about 40° C., to decrease the viscosity of the concentrated protein solution to facilitate performance of the subsequent dilution step and micelle formation. The concentrated protein solution should not be heated beyond a temperature above which the temperature of the concentrated protein solution does not permit micelle formation on dilution by chilled water. The concentrated protein solution may be subject to a further defatting operation, if required, as described in U.S. Pat. Nos. 5,844,086 and 6,005,076.

The concentrated protein solution resulting from the concentration step and optional defatting step then is diluted to effect micelle formation by mixing the concentrated protein solution with chilled water having the volume required to achieve the degree of dilution desired. Depending on the proportion of canola protein desired to be obtained by the micelle route and the proportion from the supernatant, the degree of dilution of the concentrated protein solution may be varied. With higher dilution levels, in general, a greater proportion of the canola protein remains in the aqueous phase.

When it is desired to provide the greatest proportion of the protein by the micelle route, the concentrated protein solution is diluted by about 15 fold or less, preferably about 10 fold or less.

The chilled water with which the concentrated protein solution is mixed has a temperature of less than about 15° C., generally about 3° to about 15° C., preferably less than about 10° C., since improved yields of protein isolate in the form of protein micellar mass are attained with these colder temperatures at the dilution factors used.

In a batch operation, the batch of concentrated protein solution is added to a static body of chilled water having the desired volume, as discussed above. The dilution of the concentrated protein solution and consequential decrease in ionic strength causes the formation of a cloud-like mass of highly associated protein molecules in the form of discrete protein droplets in micellar form. In the batch procedure, the protein micelles are allowed to settle in the body of chilled water to form an aggregated, coalesced, dense, amorphous sticky gluten-like protein micellar mass (PMM). The settling may be assisted, such as by centrifugation. Such induced settling decreases the liquid content of the protein micellar mass, thereby decreasing the moisture content generally from about 70% by weight to about 95% by weight to a value of generally about 50% by weight to about 80% by weight of the total micellar mass. Decreasing the moisture content of the micellar mass in this way also decreases the occluded salt content of the micellar mass, and hence the salt content of dried isolate.

Alternatively, the dilution operation may be carried out continuously by continuously passing the concentrated protein solution to one inlet of a T-shaped pipe, while the diluting water is fed to the other inlet of the T-shaped pipe, permitting mixing in the pipe. The diluting water is fed into the T-shaped pipe at a rate sufficient to achieve the desired degree of dilution.

The mixing of the concentrated protein solution and the diluting water in the pipe initiates the formation of protein micelles and the mixture is continuously fed from the outlet from the T-shaped pipe into a settling vessel, from which, when full, supernatant is permitted to overflow. The mixture preferably is fed into the body of liquid in the settling vessel in a manner which minimizes turbulence within the body of liquid.

In the continuous procedure, the protein micelles are allowed to settle in the settling vessel to form an aggregated, coalesced, dense, amorphous, sticky, gluten-like protein micellar mass (PMM) and the procedure is continued until a desired quantity of the PMM has accumulated in the bottom of the settling vessel, whereupon the accumulated PMM is removed from the settling vessel.

The combination of process parameters of concentrating of the protein solution to a protein content of at least about 200 g/L and the use of a dilution factor less than about 15, result in higher yields, often significantly higher yields, in terms of recovery of protein in the form of protein micellar mass from the original meal extract, and much purer isolates in terms of protein content than achieved using any of the known prior art protein isolate forming procedures discussed in the aforementioned U.S. patents.

By the utilization of a continuous process for the recovery of canola protein isolate as compared to the batch process, the initial protein extraction step can be significantly reduced in time for the same level of protein extraction and significantly higher temperatures can be employed in the extraction step. In addition, in a continuous operation, there is less chance of contamination than in a batch procedure, leading to higher product quality and the process can be carried out in more compact equipment.

The settled isolate is separated from the residual aqueous phase or supernatant, such as by decantation of the residual aqueous phase from the settled mass or by centrifugation. The PMM may be used in the wet form or may be dried, by any convenient technique, such as spray drying, freeze drying or vacuum drum drying, to a dry form. The dry PMM has a high protein content, in excess of about 90 wt % protein, preferably at least about 100 wt % protein (calculated as Kjeldahl N×6.25), and is substantially undenatured (as determined by differential scanning calorimetry). The dry PMM isolated from fatty oil seed meal also has a low residual fat content, when the procedures of U.S. Pat. Nos. 5,844,086 and 6,005,076 are employed, which may be below about 1 wt %.

The PMM-derived canola protein isolate predominantly consists of the 7S canola protein with minor quantities of the 12S canola protein and optionally small quantities of the 2S canola protein. In general, the PMM contains:
about 60 to about 98 wt % of 7S protein
about 1 to about 15 wt % of 12S protein
0 to about 25 wt % of 2S protein Preferably, the PMM contains:
about 88 to about 98 wt % of 7S protein
about 1 to about 10 wt % of 12S protein
0 to about 6 wt % of 2S protein The supernatant from the PMM formation and settling step contains significant amounts of canola protein, not precipitated in the dilution step, and is processed to recover canola protein isolate therefrom. The supernatant from the dilution step, following removal of the PMM, is concentrated to increase the protein concentration thereof. Such concentration is effected using any convenient selective membrane technique, such as ultrafiltration, using membranes with a suitable molecular weight cut-off permitting low molecular weight species, including the salt and other non-proteinaceous low molecular weight materials extracted from the protein source material, to pass through the membrane, while retaining canola protein in the solution. Ultrafiltration membranes having a molecular weight cut-off of about 3000 to 10,000 daltons, having regard to differing membrane materials and configuration, may be used. Concentration of the supernatant in this way also reduces the volume of liquid required to be dried to recover the protein. The supernatant generally is concentrated to a protein concentration of about 100 to about 400 g/L, preferably about 200 to about 300 g/L, prior to drying. Such concentration operation may be carried out in a batch mode or in a continuous operation, as described above for the protein solution concentration step The concentrated supernatant may be dried by any convenient technique, such as spray drying, freeze drying or vacuum drum drying, to a dry form to provide a further canola protein isolate. Such further canola protein isolate has a high protein content, in excess of about 90 wt %, preferably at least about 100 wt % protein (calculated as Kjeldahl N×6.25) and is substantially undenatured (as determined by differential scanning calorimetry).

The dried supernatant predominantly consists of the 2S canola protein with minor quantities of the 7S canola protein and optionally small quantities of the 12S canola protein. In general, the supernatant-derived canola protein isolate contains:
about 60 to about 95 wt % of 2S protein
about 5 to about 40 wt % of 7S protein
0 to about 5 wt % of 12S protein The supernatant-derived canola protein isolate preferably contains:
about 70 to about 95 wt % of 2S protein
about 5 to about 30 wt % of 7S protein
0 to about 2 wt % of 12S protein If desired, at least a portion of the wet PMM may be combined with at least a portion of the concentrated supernatant prior to drying the combined protein streams by any convenient technique to provide a combined canola protein isolate composition according to one invention. The relative proportions of the proteinaceous materials mixed together may be chosen to provide a resulting canola protein isolate composition having a desired profile of 2S/7S/12S proteins. Alternatively, the dried protein isolates may be combined in any desired proportions to provide any desired specific 2S/7S/12S protein profiles in the mixture and thereby provide a composition according to the invention. The combined canola protein isolate composition has a high protein content, in excess of about 90 wt %, preferably at least about 100 wt %, (calculated as Kjeldahl N×6.25) and is substantially undenatured (as determined by differential scanning calorimetry).

In another alternative procedure, where a portion only of the concentrated supernatant is mixed with a part only of the PMM and the resulting mixture dried, the remainder of the concentrated supernatant may be dried as may any of the remainder of the PMM. Further, dried PMM and dried supernatant also may be dry mixed in any desired relative proportions, as discussed above.

By operating in this manner, a number of canola protein isolates may be recovered, in the form of dried PMM, dried supernatant and dried mixtures of various proportions by weight of PMM-derived canola protein isolate and supernatant-derived canola protein isolate, generally from about 5:95 to about 95:5 by weight, which may be desirable for attaining differing functional and nutritional properties based on the differing proportions of 2S/7S/12S proteins in the compositions.

As an alternative to dilution of the concentrated protein solution into chilled water and processing of the resulting precipitate and supernatant as described above, protein may be recovered from the concentrated protein solution by dialyzing the concentrated protein solution to reduce the salt content thereof. The reduction of the salt content of the concentrated protein solution results in the formation of protein micelles in the dialysis tubing. Following dialysis, the protein micelles may be permitted to settle, collected and dried, as discussed above. The supernatant from the protein micelle settling step may be processed, as discussed above, to recover further protein therefrom. Alternatively, the contents of the dialysis tubing may be directly dried. The latter alternative procedure is useful where small laboratory scale quantities of protein are desired.

The relative quantities of the respective proteins in any given protein isolate may be determined by any convenient analytical techniques, such as an analytical separation technique. The most common of these techniques uses selective media in a column that permits separation based on size. For gel permeation chromatography (GPC) applications, spherical gel-like materials are used. Where pressure is used, as in high pressure liquid chromatography (HPLC), then a rigid media is used. The latter technique also is known as size exclusion chromatography (SEC). The results obtained using such techniques on samples of canola protein isolate prepared as described herein are contained in the Examples below.

The procedure of mass spectroscopy (MS) may be used to identify and analyze protein samples, including the 2S, 7S and 12S proteins of canola described herein. In electron spray ionization (ESI) mass spectroscopy, the protein is bombarded with low energy electrons and charged fragments or species formed from the collision are detected. In particular, a matrix assisted laser desorption ionization (MALDI) mass spectrometer may be used wherein there is laser vaporization of a dry sample of material for analysis that contains a specific molecular matrix. The matrix contains a compatible, small molecular weight organic molecule that protects the biopolymer under analysis sufficiently to reduce the number of ionized species produced from the laser impact energy.

Data derived from protein isolate samples as described herein suggests that the 2S protein is not stable to electron bombardment by ESI-MS and readily fragments into numerous polypeptide fragments, which include 4 kDa, 10 kDa and 21 kDa species. Using MALDI-MS, however, produced an intact 2S fraction with a molecular mass of close to 14,000 daltons.

The 7S protein in the PMM-derived protein isolate also produced a large number of sub-10 kDa fragments, suggesting molecular instability to electron bombardment in ESI-MS. In addition, a 21 kDa species was identified in analysis of 7S protein from PMM-derived canola protein isolate, but this species was absent in the 7S protein from supernatant-derived canola protein isolate.

ESI-MS analysis of the 7S protein from PMM-derived canola protein isolate also indicated six protein molecular masses ranging from 126 to 166 kDa while the 7S protein from supernatant-derived canola protein isolate indicated one large species at 167 kDa.

MALDI-MS analysis results described herein indicate that the 2S protein has a molecular mass between 13,960 and 14,250 da and is quite resistant to mild acid treatment. The 7S and 12S proteins are composed of the same building blocks with a basic subunit of 48,200 to 48,400 da. The 7S protein has a molecular mass of three subunits or about 145,000 da molecular mass while the 12S protein contains 6 subunits with a combined molecular mass of about 290,000 da Acid hydrolysis of the 7S and 12S proteins did not produce 2S protein and produced almost identical results, confirming that these two globular proteins are obtained from the same subunit.

The individual 2S, 7S and 12S proteins may be isolated and purified from the respective protein isolates by any conventional procedure, including analytical high pressure liquid chromatography (HPLC) for smaller quantities of protein and preparative HPLC for larger quantities. Other procedures achieving composition on the basis of molecular mass may be used. The 2S protein generally is isolated and purified from the supernatant-derived canola protein isolate while the 7S and 12S proteins generally are isolated and purified from the PMM-derived canola protein isolate. The canola protein isolate is solubilized, such as by using saline, and then passed through the HPLC column. The HPLC separated proteins contained in fractions of eluant containing one of the proteins, usually are subjected to ultrafiltration to reduce the volume of eluant followed by protein isolate dialysis to reduce the residual salt content in the proteins. The dialyzed material may be dried to provide dried isolated and purified individual canola protein.

DESCRIPTION OF PREFERRED EMBODIMENTS

Referring to FIG. 1, there is illustrated schematically a flow sheet of a batch process for the preparation of canola protein isolates. Canola oil seed meal and aqueous extraction medium are fed by line 10 to an extraction vessel 12 wherein the oil seed meal is extracted and an aqueous protein solution is formed. The slurry of aqueous protein solution and residual oil seed meal is passed by line 14 to a vacuum filter belt 16 for separation of the residual oil seed meal which is removed by line 18. The aqueous protein solution then is passed by line 20 to a clarification operation 22 wherein the aqueous protein solution is centrifuged and filtered to remove fines, which are recovered by line 24.

The clarified aqueous protein solution is pumped by line 26 through ultrafiltration membrane 28 to produce a concentrated protein solution as the retentate in line 30 with the permeate being recovered by line 32. The concentrated protein solution is passed into a precipitation vessel 34 containing cold water fed by line 36. Protein micellar mass formed in the precipitation vessel 34 is removed by line 38 and passed through a spray dryer 40 to provide dry canola protein isolate 42.

Supernatant from the precipitation vessel 34 is removed by line 44 and pumped through ultrafiltration membranes 46 to produce a concentrated protein solution as the retentate in line 48 with the permeate being removed by line 50. The concentrated protein solution is passed through a spray dryer 52 to provide further dry canola protein isolate 54.

As an alternative, the concentrated protein solution in line 48 may be passed by line 56 to mix with the protein micellar mass before the mixture then is dried in spray dryer 40.

Figure 2:
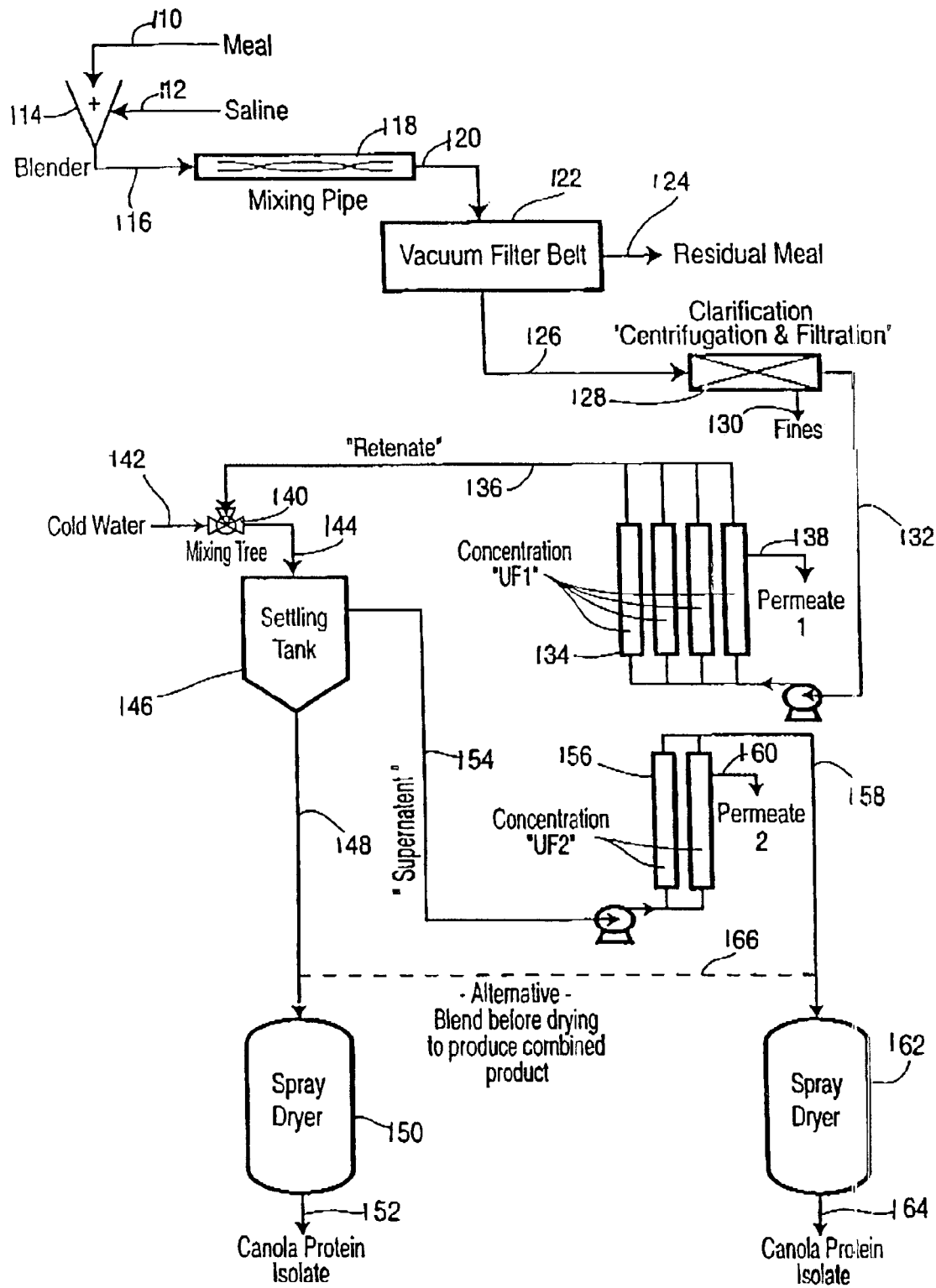
FIG. 2 is a schematic flow sheet of a continuous procedure for producing canola protein isolates of differing protein profiles according to another embodiment of the invention.

Referring to FIG. 2, there is illustrated schematically a flow sheet of a continuous process for the preparation of canola protein isolates. Canola oil seed meal and aqueous extraction medium are fed by lines 110 and 112 respectively to a blender 114 wherein the oil seed meal and aqueous extraction medium are mixed and the mixture is passed by line 116 to a mixing pipe 118. In the mixing pipe 118, the oil seed meal is extracted and an aqueous protein solution is formed. The slurry of aqueous protein solution and residual oilseed meal is passed by line 120 to a vacuum filter belt 122 for separation of the residual oil seed meal which is removed by line 24. The aqueous protein solution then is passed by line 126 to a clarification operation 128 wherein the aqueous protein solution is centrifuged and filtered to remove fines, which are recovered by line 130.

The clarified aqueous protein solution is pumped by line 132 through ultrafiltration membranes 134 sized to provide the desired degree of concentration of the aqueous protein solution to produce a concentrated protein solution as the retentate in line 136 with the permeate being recovered by line 138. The concentrated protein solution is passed into the inlet of a mixing tee 140, with cold water being fed thereto by line 142 in a volume sufficient to achieve the desired degree of dilution. The resulting solution is fed by line 144 to a settling tank 146 to permit the protein micellar mass to settle. Protein micellar mass settled in the settling vessel 146 is removed by line 148 from time to time and passed through a spray dryer 150 to provide dry canola protein isolate 152.

Supernatant from the settling tank is removed by line 154 and pumped through ultrafiltration membranes 152 to produce a concentrated protein solution as the retentate in line 158 with the permeate being removed by line 160. The concentrated protein solution is passed through a spray dryer 162 to provide further dry canola protein isolate 164.

As an alternative, the concentrated protein solution in line 158 may be passed by line 166 to mix with the protein micellar mass before the mixture then is dried in spray dryer 150.

EXAMPLES

Example 1

This Example illustrates the procedure adopted to provide the canola protein isolates of the invention.

'a' kg of commercial canola meal was added to 'b' L of 0.15 M NaCl solution at ambient temperature, agitated for 30 minutes to provide an aqueous protein solution having a protein content of 'c' g/L. The residual canola meal was removed and washed on a vacuum filter belt. The resulting protein solution was clarified by centrifugation to produce 'd' L of a clarified protein solution having a protein content of 'e' g/L.

A 'f' L aliquot of the protein extract solution was reduced in volume to 'g' L by concentration on an ultrafiltration system using 'h' dalton molecular weight cut-off membranes. The resulting concentrated protein solution had a protein content of 'i' g/L.

The concentrated solution at 'j' ° C. was diluted 'k' into 4° C. water. A white cloud formed immediately and was allowed to settle. The upper diluting water was removed and the precipitated, viscous sticky mass (PMM) was recovered from the bottom of the vessel in a yield of 'l' wt % of the extracted protein. The dried PMM-derived protein was found to have a protein content of 'm'% (N×6.25) d.b. (Percentage nitrogen values were determined using a Leco Fl'528 Nitrigen Determinator). The product was given designation 'n''.

The parameters 'a' to 'n' for five PMM-derived canola protein isolates are given in the following Table I:

TABLE 1

| n | BW-AL017-B14-02A-C300 | BW-AL017-B20-02A-C300 | BW-AL017-D29-C300 | BW-AL021-I24-02A-C300 | BW-AL021-130-02A-C300 |
|---|---|---|---|---|---|
| a | 150 | 150 | 150 | 150 | 150 |
| b | 1000 | 1000 | 1000 | 1000 | 1000 |
| c | 22.0 | 22.6 | 20.2 | 29.3 | 30.0 |
| d | 1000 | 1040 | 1040 | 1080 | 1080 |
| e | 15.4 | 15.3 | 14.6 | 20.8 | 19.2 |
| f | 600 | 500 | 1040 | 1080 | 1080 |
| g | 18 | 17 | 44 | 47.5 | 48.0 |
| h | 3000 | 3000 | 5000 | 5000 | 5000 |
| i | 289 | 236 | 225 | 311 | 218 |
| j | 31 | 32 | 30 | 24 | 19 |
| k | 1:15 | 1:15 | 1:15 | 1:15 | 1:15 |
| l | 19 | 22 | 29 | 35 | 20 |
| m | 105.8 | 102.9 | 103.2 | 105.4 | 103.0 |

The removed diluting water was reduced in volume by ultrafiltration using a 'o' dalton molecular weight cut-off membrane to a protein concentration of 'p' g/L. The concentrate was dried. With the additional protein recovered from the supernatant, the overall protein recovery was 'q' wt %. The dried protein which was formed had a protein content of 'r' wt % (N×6.25) d.b.

The product was given designation 's'. The parameters 'o' to 's' for five supernatant-derived canola protein isolates are given in the following Table II:

TABLE II

| s | BW-AL017-B14-02A-C200 | BW-AL017-B20-02A-C200 | BW-AL017-D29-C200 | BW-AL021-I24-02A-C200 | BW-AL021-130-02A-C200 |
|---|---|---|---|---|---|
| o | 3000 | 3000 | 5000 | 5000 | 5000 |
| p | 60.8 | 57.8 | 121.8 | 78.0 | 68.1 |
| q | 31.0 | 33.0 | 45 | 49 | 33 |
| r | 97.8 | 103.6 | 100.8 | 103.7 | 97.8 |

Example 2

This Example illustrates analysis of the PMM-derived and supernatant-derived canola protein isolates of Example 1.

A Gradi-Frac (Pharmacia Amersham) protein separator having 100 cm column and Sephacryl 300 HR media (Sephacryl 300 HR is a dextran polymer, cross-linked with methylene bis-acrylamide that permits fractionation of globular proteins with 10,000 to 1,500,000 dalton size) was run with a series of standards of protein origin to determine the residence time (RT) of each component, as measured at A280 nm, at an elution flow rate of 1.0 mL/min. Saline solution, pH adjusted and containing sodium azide as an antibacterial agent, was used as the column solvent. Eluant was collected in test tubes on an autosample rack with each test tube holding 5 mL of liquid. Relative protein fractions were calculated by peak area, obtained by multiplying half-base times peak height at maximum.

An analytical Varian high pressure liquid chromatography column (HPLC), using a 300×7.8 mm BioSep S3000 Size Exclusion Chromatography (SEC) column containing hydrophilic-bonded silica rigid support media, 5-micron diameter, 290-Angstrom pore size, capable of separating globular proteins from 5,000 to 700,000 dalton size, was run using the same BioRad protein standards as with the Gradi-Frac system. The BioRad proteins cover a range from 17,000 daltons (myoglobulin) to 670,000 daltons (thyroglobulin) with Vitamin B12 added as a low molecular mass marker at 1,350 daltons. Each component is measured at 280 nm at an elution flowrate of 1.0 mL/min. Saline solution, pH adjusted and containing sodium azide as an antibacterial agent, was used as the column solvent and to dissolve dry samples. Eluant was discarded after UV detection as no more than 50 microliters of sample are required per run. The HPLC Prostar system automatically calculated retention times and peak areas and printed out a summary report.

Samples of the PMM-derived and supernatant-derived canola protein isolates, prepared as described in Example 1 for lots BW-AL-017-B14-02A-C300 and BW-AL017-B20-02A-C300, were run on each column. The peak area counts were converted to percentage for each peak. All peaks on different runs were taken into calculation and then the three major protein fractions, 12S, 7S and 2S, were recalculated separately.

In addition, standard curves, derived from the BioRad standard were used to calculate approximate molecular weights for the three protein fractions, 12S, 7S and 2S, for runs made using both GPC and HPLC. The Gradi-Frac system contains more variability than the HPLC system which results from the larger sample size (1 milliliter versus 25 microliters) and column diameter, the manual calculation of the Gradi-Frac results and the run time differences (25 minutes for the HPLC versus 5 hours for the Gradi-Frac). In addition, the Gradi-Frac system uses volume as the measure of protein retention while HPLC uses time.

The variation in the data shown in the Tables III and IV below reflects the differences indicated above. The HPLC system statistically is better (lower variability) than the Gradi-Frac system. The Gradi-Frac system does have the advantage of providing individual sample fractions that can be further tested (for example, using mass spectrometry), unlike the HPLC system.

The results obtained are set forth in the following Table III for the PMM-derived canola protein isolate (CPI) and Table IV for the supernatant-derived canola protein isolate (CPI):

TABLE III

| | | | PMM-Derived CPI | | | | | | HPLC GPC Protein Ratios | | | | |
| | | | Protein Fractions: | | | % of all Peaks | | | 2, 7, 12S | Others | Calculated Molecular | | |
| Protein | | | % | % | % | % | % | % | % of all | % of all | Weights in kilo-Daltons | | |
| Type: | Meal: | Run#: | 12S | 7S | 2S | 12S | 7S | 2S | Peaks | Peaks | 12S | 7S | 2S |
| HPLC-SEC | | | | | | | | | | | | | |
| PMM | AL017 | B14 | 6% | 94% | 0.1% | 6% | 92% | 0% | 98% | 2% | 341 | 147 | 12.1 |
| PMM | AL017 | B20 | 6% | 94% | 0.1% | 6% | 92% | 0% | 98% | 2% | 342 | 146 | 11.5 |
| | | Average | 6% | 94% | 0% | 6% | 92% | 0% | 98% | 2% | 342 | 146 | 11.8 |
| | | s.d | 0% | 0% | 0% | 0% | 0% | 0% | 0% | 0% | 1 | 1 | 0.4 |
| Gradi-Frac GPC | | | | | | | | | | | | | |
| PMM | AL017 | B14 | 8% | 82% | 9% | 8% | 82% | 9% | 99% | 1% | 354 | 152 | 8.7 |
| PMM | AL017 | B20 | 9% | 89% | 2% | 9% | 88% | 2% | 99% | 1% | 40.3 | 163 | 8.6 |
| | | Average | 9% | 86% | 6% | 8% | 85% | 6% | 99% | 1% | 378 | 158 | 8.6 |
| | | s.d. | 0% | 5% | 5% | 0% | 5% | 5% | 0% | 0% | 35 | 8 | 0.0 |

Molecular Weight calculations based on BioRad GPC Standards containing animal proteins.

TABLE IV

| | | | Supernatant-Derived CPI | | | | | | HPLC GPC Protein Ratios | | | | |
| | | | Protein Fractions: | | | % of all Peaks | | | 2, 7, 12S | Others | Calculated Molecular | | |
| Protein | | | % | % | % | % | % | % | % of all | % of all | Weights in kilo-Daltons | | |
| Type: | Meal: | Run#: | 12S | 7S | 2S | 12S | 7S | 2S | Peaks | Peaks | 12S | 7S | 2S |
| HPLC-SEC | | | | | | | | | | | | | |
| Supernatant | AL017 | B14 | 0% | 25% | 75% | 0% | 25% | 75% | 99% | 1% | none | 126 | 13.9 |
| Supernatant | AL017 | B20 | 0% | 24% | 76% | 0% | 24% | 76% | 99% | 1% | none | 135 | 15.2 |
| | | Average | 0% | 24% | 76% | 0% | 24% | 76% | 99% | 1% | | 130 | 14.5 |
| | | s.d | 0% | 1% | 1% | 0% | 1% | 1% | 0% | 0% | | 6 | 1.0 |
| Gradi-Frac GPC | | | | | | | | | | | | | |
| Supernatant | AL017 | B14 | 0% | 37% | 63% | 0% | 29% | 50% | 79% | 21% | none | 147 | 10.6 |
| Supernatant | AL017 | B20 | 0% | 37% | 63% | 0% | 29% | 50% | 79% | 21% | none | 147 | 10.6 |
| | | Average | 0% | 37% | 63% | 0% | 28% | 48% | 76% | 24% | | 150 | 10.8 |
| | | s.d. | 0% | 0% | 0% | 0% | 1% | 3% | 4% | 4% | | 4 | 0.3 |

Molecular Weight calculations based on BioRad GPC Standards containing animal proteins.

As may be seen from the data presented in Table III, the PMM-derived samples contained a large amount of 7S protein with minor percentages of 2S and 12S proteins.

As may be seen from Table IV, 12S protein is substantially absent from the supernatant-derived canola protein isolate while the predominant protein was the 2S protein, with quantities of 7S protein being present.

The calculated molecular weights for the HPLC runs were lower for the 12S and 7S proteins but higher for the 2S protein. This apparent discrepancy may be due, in part, to difficulties in accurately pinpointing the peak maximums for the GPC runs, which were all done by hand.

The GPC calculated weight of 385,000 dalton for 12S is higher than reported in the literature for canola cruciferin, which range from 300,000 to 310,000 da. The GPC and HPLC calculated molecular weights for 7S are similar and close to the reported value of about 150,000 da. The HPLC estimate for 2S is higher than the GPC average and both less than the reported value for napin of 14,000 da.

As may be seen from the above data, the PMM-derived canola protein isolate in the samples tested contains the 7S fraction in amounts ranging from 82 to 89% (by GPC) and 94% (by HPLC). As mentioned above, the HPLC procedure is faster and is considered to be more accurate than GPC. Based on the three protein fraction areas, it is considered that the PMM-derived samples contain:

about 88 to about 98 wt % of 7S protein
about 1 to about 10 wt % of 12S protein
0 to about 6 wt % of 2S protein Similarly, for the supernatant-derived samples, based on the three protein fraction areas, it is considered that these samples contain:

about 70 to about 95 wt % of 2S protein
about 5 to about 30 wt % of 7S protein
0 to about 2 wt % of 12S protein The term "Protein Fraction" as used above is defined as the area of a peak at HPLC (or GPC) Retention Time that generates calculated molecular weights in the ranges discussed above, according to acceptable GPC/HPLC protein standards such as available from BioRad. These peaks may contain other components, but as long as they lie in an acceptable range of the target molecular weights, their presence would be irrelevant.

An acceptable target of molecular weights, based on the information contained in this Example, would appear to be:

12S: 300,000 to 360,000 da
7S: 125,000 to 160,000 da
2S: 9,000 to 15,000 da

Example 3

This Example shows the effects of certain parameters on protein extraction.

In a first set of experiments, 50 g samples of canola oil seed meal which had been low temperature toasted (LT meal) at 100° C. to remove residual solvent were added to 500 mL samples of 0.05 M or 0.10 M NaCl solution at room temperature (20° C.) and stirred for 15 minutes. The slurry was centrifuged at 5000×g for 10 minutes to extract and spent meal.

In a second set of experiments, 500 mL of water with no salt added was first heated to 60° C. on a hot plate stirrer and then 50 g of canola oil seed meal which had been low temperature toasted at 100° C. to remove residual solvent were added and stirred for 15 minutes while the temperature was maintained. The extract was separated from the spent meal by centrifugation at 5000×g for 10 minutes.

The protein concentration of the various aqueous protein solutions obtained in these experiments were determined and appear in the following Table V:

TABLE V

| | Protein Concentrations in Extracts (wt %) | | |
|---|---|---|---|
| | 0.05 M saline | 0.10 M saline | 60° C. water |
| LT meal | 1.11 | 1.44 | 0.98 |

The protein extractability from the meals was determined from the protein concentration data of Table V and this data is presented in Table VI:

TABLE VI

| | Protein Extractability (wt %)* | | |
|---|---|---|---|
| | 0.05 M saline | 0.10 M saline | 60° C. water |
| LT meal | 28.6 | 37.4 | 25.5 |

*Defined as percentage of the amount of protein extracted of the total amount of protein in the meal.

Samples of extracts prepared as described in this Example were run on each of the HPLC and SEC columns described in Example 2. The peak area counts were converted to percentage for each peak. All peaks on different runs were taken into calculation and then the three major protein fractions 12S, 7S and 2S, were recalculated separately. The results obtained are shown in the graphical data of FIGS. 2 to 4.

Each chromatogram showed a distinct peak representing 7S canola protein fraction and a small bump of 12S canola protein fraction. The peak for the 2S canola protein fraction was present among peaks for other components of the extract. The peaks in the lower molecular weight end of the chromatogram were not properly identified, but likely correspond to non-protein nitrogenous compounds, such as short peptides and free amino acids, as well as other meal components, such as phenolic compounds, glucosinolates and phytates.

Example 4

This Example illustrates analysis of canola protein isolate samples.

Gel permeation chromatography as described in Example 2 was performed on samples of spray dried canola protein isolate samples from lots BW-AL017-D29-C200 and BW-AL017-D29-C300, prepared as described in Example 1, which produced four protein fractions that were labelled 2S, >2S, 7S and 12S, with the 2S and possibly >2S fractions representing small, water soluble albumins and the 7S and 12S protein representing the more hydrophobic, less-water soluble globulins.

These fractions and mild acid-treated samples were analyzed by MALDI mass spectroscopy and produced the following results:

2S Fraction:

Analysis using MALDI-MS indicated a molecular mass of close to 14,000 daltons. A narrow band peak was observed with the top of the peak splintered, with the major spike lying between 13,960 da and 14,250 da, a difference of 2 to 3 amino acids, which could be indication of different protein isozymes.

Acid treatment of the 2S fraction in 5% acetic acid for 24 hours did not reveal any smaller polypeptide species to a low limit cut-off of 8,000 da, indicating a resistance of the 2S protein to mild acidification.

>2S Fraction:

The MS scans of this material indicated a small peak at about 13,950 to 13,990 da, attributable to 2S protein, and a major peak at 13,380 to 13,410 da of unknown origin. The fraction also contained a significant but less intense peak at between 17,160 and 17,260 da, also of unknown origin.

Mild acid treatment of the latter fraction with 5% acetic acid for 24 hours reduced only the major peak at 13,400 da, with some minor components appearing at about 7,000 to 8,000 da, possibly hydrolysis products. The 2S peak did not appear diminished.

7S Fraction:

The MS scans of this material showed the most significant peak to occur at between 48,150 and 49,950 da with the major spike at about 48,400±100 da. A much less intense and broader peak appeared with two spikes at approximately 95,940 da and 97,510 da respectively, which indicates the presence of a small quantity of protein containing two subunits. The analyses carried out in Example 2 suggest a molecular mass of about 150,000 da for the 7S protein while the MALDI analysis herein indicates a slightly lower molecular mass of about 145,000 da.

A minor component appeared at 13,420 da, in the area of the major >2S fraction peak, but not at 14,000 da. A major triplet of peak appeared at between 6,975 and 17,905 da. These peaks are probably attributable to a major polypeptide in the protein subunit and was also present in the >2S fraction but not the 2S fraction.

Acid treatment of the 7S fraction with 1% acetic acid for 24 hours left the major species intact at 48,310-da with a lesser peak at 45,750 da (possible loss of a small polypeptide). New peaks appeared at 16,310 da, 22,710 da and 24,070 da and likely represent hydrolysis products.

Further acid treatment of the 7S fraction was effected using 20% formic acid. Scans were taken after one hour of treatment and again after three days exposure to the formic acid.

A new species appeared at about 26,300 da after the one hour exposure and the other peaks were approximately where noted for the 5% acetic acid treatment. Exposure for three days led to a drop in the peak intensity for the major subunit (48,260 da) with a rise in the major peaks at 16,315 da and 17.850 da.

Scans below 9,000 da revealed a characteristic pattern of six peaks at 4,490 da, 5,720 da, 6,530 da, 7,030 da and 7,330 da, although the peak at 4,490 da increased significantly by the third day.

12S Fraction:

MALDI-MS analysis of the 12S fraction produced a major peak centered at between 48,150 and 48,200 da, representing the major protein subunit. The major downfield peak occurred at 94,960 da with other lesser peaks at 64,620 da, 77,540 da, 126,990 da and 143,280 da. The large molecular mass peaks were not well defined and can only approximate the true molecular masses. The major downfield peak is close to two times the subunit molecular mass while the broad peak at 143,280 da is close to three times the subunit mass.

Other significant peaks appear at about 13,400 da, 16,400 da, 17,900 da and 29,000 to 29,700 da, which are probably some of the polypeptides that make up to protein subunits.

Acid treatment of the 12S fraction with 5% acetic acid for 24 hours produced a profile nearly identical to that for the 7S fraction and described above. Treatment with 20% formic acid after three days showed a loss of the major subunit at 48,100 da and a rise in the 17,900 da species.

Scans below 9,000 da were almost identical to the 7S hydrolysis after one hour in 20% formic acid, with six major peaks at 4,480 da, 5,730 da, 6,510 da, 6,650 da, 7,020 da and 7,310 da. The peak at 4,480 da did not increase significantly by the third day of formic acid treatment unlike the results for the 7S fraction.

Having regard to the results of the MALDI-MS analysis reported in this Example, it can be concluded that:

(a) the 2S protein has a molecular mass of between 13,960 and 14,250 da, in line with published results of close to 14,000 da and is quite resistant to mild acid treatment.

The 7S and 12S proteins are composed of the same building blocks with a basic subunit in the 48,200 to 48,400 da range. The 7S protein has a molecular mass of three subunits or about 145,000 da and the 12S protein contains 6 subunits with a combined molecular mass of about 290,000 da. These values are lower than those obtained by the GPL and HPLC SEC molecular mass calculations in Example 2, but those results are based on animal standards.

(c) Acid hydrolyses of the 7S and 12S proteins do not produce the 2S protein.

(d) Acid hydrolysis of the two globular proteins gave almost identical results, confirming that the two proteins were obtained from the same subunit.

Example 5

This Example illustrates preparative high pressure liquid chromatography (HPLC).

A Varian Preparative high pressure liquid chromatography system (prep-HPLC), using a 300×21.20 mm Phenomenex BioSep S3000 size Exclusion chromatography (SEC) main column, containing hydrophilic-bonded silica rigid support media, 5-micron diameter, 290-Angstrom pore size, was used for the fractionation of the canola proteins. A disposable pre-column, containing the same packing and with a size of 60×21.20 mm, was attached ahead of the main column.

Each analyte was monitored at 280 nm at an elution rate between 6 mL/minute and 8 mL/minute. The upper pressure limit of 1,000 psi on the column was not exceeded at these flow rates. Saline solution, containing sodium azide as an antibacterial agent, was used as the column mobile phase and was also used to dissolve the dry canola protein samples. Eluant was collected in a Varian Model 701 Fraction collector. Run times ranged from 12 minutes to 15 minutes depending on the sample.

The sample injection volume was between 1.0 and 1.5 mL for a sample concentration of between 2.0% and 3.0% by dry weight of protein isolate, or 20 mg to 45 mg solids per injection. The capacity of the column can be exceeded beyond 1.5 mL, dependent on sample type and concentration. Sample preparations were stirred for a minimum of 30 minutes before centrifugation at 10,000 rpm for 20 minutes. The supernatant was then vacuum-filtered through a minimum of a 0.45-micron membrane disk.

Although the system can be run continuously over a 24-hour period, this was not usually done as a cleaning procedure, involving acetonitrile in water, was required daily to remove impurities from the column. Even so, 80 to 100 runs can usually be made each day, with between 0.5 and 1.2 grams of analyte collected.

Samples were prepared from PMM-derived and supernatant-derived canola protein isolates, including the following: BW-AL-017-D29-02A-C200, BW-AL021-I24-02A-C200, BW-AL021-I30-02A-C200, BW-AL-017-D29-02A-C300, BW-AL021-I24-02A-C300 and BW-AL021-I30-02A-C300, prepared as described in Example 1.

PMM (C300) samples were used for the collection of 7S and 12S proteins, while supernatant-derived (C200) samples were primarily used to collect 2S. Fraction aliquots were tested on the Varian Analytical SEC-HPLC for purity. The eluant protein levels were typically less than 0.3 wt % (N×6.25) or less than 2.0 Absorbance Units at 280 nm, and the salt content was normally between 0.5 wt % and 0.7 wt % NaCl as determined by conductivity.

Example 6

This Example illustrates ultrafiltration and dialysis of the fractions collected in Example 5.

Ultra-filtration, followed by dialysis, are both effected to reduce the large eluant volume and the high salt-to-protein ratio. The dilute eluant from the Varian Preparative HPLC system described in Example 5 was concentrated in two Amicon Series 8000 Ultra-filtration stirred cell units, each with a rated maximum capacity of 400 mL of volume.

Each unit was fitted with a 76 mm diameter membrane with selective molecular size cut-off. For 2S protein, membranes used included: Ultracel Amicon YM1 UF disc with regenerated cellulose, 1,000 NMWL (Nominal Molecular Weight Limit), #13342, and Ultracel Amicon YM10 UF discs of regenerated cellulose, 10,000 NMWL, #13642.

For the larger 7S and 12S globular proteins, higher NMWL membranes were used: Biomax PBQK UF discs of polyethylene sulfone (PES), 50,000 NMWL, #PBQK 07610, or Biomax PBHK UF discs of PES, 100,000 NMWL, #PBHK 07610.

Higher NMWL membranes produced slight losses in protein retention, called the Retentate, but also removed lower-molecular-weight impurities that are weakly associated with the protein. Higher NMWL cut-offs also reduced the UF operating times. Typical run times for 1,200 ml of HPLC sample on the two UF units were 4 to 5 hours.

In a typical run, sample was added to the 325 mL line in each unit. With stirring, the levels rise to about 375 mL. The units were sealed and pressure was applied to 60 psi, while the samples were stirred. When the Retentate inside the units dropped to about 100 mL, the pressure was released and additional sample was added to each unit. This process continued until the entire sample was added. The final Retentate was concentrated to between 75 mL and 100 mL inside each cell.

The eluant, called the Permeate, was removed from each unit and measured for salinity by conductivity, and for relative protein content by absorbance at 280 nm using a 1-cm cell on a UV-Visible UltraSpec 1000E Spectrophotometer. A mass balance was calculated to provide information on the efficiency of the UF membranes. UF Permeate and final Retentate samples were tested by analytical SEC-HPLC, as described in Example 2, for purity.

The Ultra-Filtration Retentate was poured into Spetra/Por 7 Dialysis membranes, 1,000 MWCO (Molecular Weight Cut-Off), 24.2 mm diameter, #132104. Each piece of tubing was cut to about 300 mm. The filled membranes were then placed into sealed 4-liter bottles containing RO water. The RO water was replaced twice before the dialyzed samples were removed from the tubes and placed in pans for freezing at −65° C. Final salinities were typically below 0.1 wt % based on conductivity.

The frozen samples were then placed into the Virtis SRCX-15 Freeze Dryer. Drying times were variable, dependent upon water loading. The dried samples were removed from the pans and weighed prior to distribution for analyses.

Example 7

This Example illustrates amino acid analysis.

Individual ultra-filtered, dialyzed and freeze-dried canola proteins 2S, 7S and 12S, prepared as described in Examples 5 and 6, have been analyzed for amino acid content. The 2S sample was derived from canola protein isolate AL021-I30-02A C200 while the 7S and 12S proteins were derived from canola protein isolate AL017-D29-02A C300.

The amino acid analysis is set forth in the following Table VII:

TABLE VII

| | | g/100 g dry matter | | |
|---|---|---|---|---|
| Amino Acid MW (1) | Amino Acid | AL021-I30-02A 2S | AL017-D29-02A 7S | AL017-D29-02A 12S |
| 133.1 | Aspartic | 3.18 | 11.60 | 3.02 |
| 119.1 | Threonine | 2.70 | 3.34 | 1.00 |
| 105.1 | Serine | 3.84 | 4.52 | 1.23 |
| 204.2 | Tryptophan | 1.16 | 1.42 | 0.40 |
| 146.1 | Glutamic | 25.10 | 21.50 | 5.91 |
| 75.1 | Glycine | 3.91 | 5.44 | 1.45 |
| 89.1 | Alanine | 3.67 | 4.47 | 1.13 |
| 121.1 | Cystine | 4.13 | 1.19 | 0.34 |
| 117.1 | Valine | 4.02 | 5.92 | 1.55 |
| 149.2 | Methionine | 2.55 | 1.74 | 0.41 |
| 131.2 | Isoleucine | 2.89 | 5.12 | 1.31 |
| 131.2 | Leucine | 6.13 | 8.70 | 2.31 |
| 181.2 | Tyrosine | 1.14 | 2.67 | 0.70 |
| 165.2 | Phenylalanine | 2.43 | 5.01 | 1.23 |
| 155.2 | Histidine | 2.58 | 1.60 | 0.45 |
| 146.2 | Lysine | 5.92 | 3.17 | 0.83 |
| 174.2 | Arginine | 5.99 | 8.02 | 2.13 |
| 115.1 | Proline | 9.02 | 5.83 | 1.68 |
| | Sum: | 90.36 | 101.26 | 27.24 |
| | Avg. aa MW (1) | 134.61 | 134.86 | 134.77 |
| | Anhydrous MW (2) | 116.59 | 116.85 | 116.75 |

Note:
(1): Molecular Weight of "free" amino acids.
(2): Weight Average Molecular Weight of polymeric amino acids.

The values presented in Table VII represent amino acids on the basis of grams per 100 grams dry weight. The 12S sample contained residual salt, even after ultrafiltration, accounting for the low total amino acid weight in the samples in comparison to the 7S and 2S samples The data was adjusted to the basis of 100 grams of amino acid and the revised data is shown in the following Table VIII:

TABLE VIII

| Amino Acid Summary: g/100 g Amino Acids | | | | |
|---|---|---|---|---|
| Hydrophobicity: Gibb's: kJ/100 g: | Amino Acid | AL021-I30-02A 2S | AL017-D29-02A 7S | AL017-D29-02A 12S |
| — | Aspartic* | 3.5 | 11.5 | 11.1 |
| 1.40 | Threonine$^e$ | 3.0 | 3.3 | 3.7 |
| — | Serine | 4.2 | 4.5 | 4.5 |
| 6.96 | Tryptophan$^e$ | 1.3 | 1.4 | 1.5 |
| — | Glutamic* | 27.8 | 21.2 | 21.7 |
| — | Glycine | 4.3 | 5.4 | 5.3 |
| 2.35 | Alanine | 4.1 | 4.4 | 4.3 |
| 3.45 | Cystine$^e$ | 4.6 | 1.2 | 1.2 |
| 5.35 | Valine$^e$ | 4.4 | 5.8 | 5.7 |
| 3.64 | Methionine$^e$ | 2.8 | 1.7 | 1.5 |

TABLE VIII-continued

Amino Acid Summary: g/100 g Amino Acids

| Hydrophobicity: Gibb's: kJ/100 g: | Amino Acid | AL021-I30-02A 2S | AL017-D29-02A 7S | AL017-D29-02A 12S |
|---|---|---|---|---|
| 9.56 | Isoleucine[e] | 3.2 | 5.1 | 4.8 |
| 7.32 | Leucine[e] | 6.8 | 8.6 | 8.5 |
| 5.30 | Tyrosine | 1.3 | 2.6 | 2.6 |
| 6.33 | Phenylalanine[e] | 2.7 | 4.9 | 4.7 |
| 1.35 | Histidine[e] | 2.9 | 1.6 | 1.7 |
| — | Lysine[e] | 6.6 | 3.1 | 3.2 |
| — | Arginine[e] | 6.6 | 7.9 | 7.8 |
| 9.44 | Proline | 10.0 | 5.8 | 6.2 |
| | Sum: | 100.0 | 100.0 | 100.0 |
| | Sum essential aa: | 44.8 | 44.7 | 44.3 |
| | % Hydrophobic aa: | 46.9 | 46.4 | 46.3 |
| | Hydroph. kJ/100 g: | 274.5 | 279.3 | 277.7 |

[e]= 11 essential amino acids
aa= amino acids
*Glutamic acid and aspartic acid are mostly amidated to glutamine and asparagine As may be seen from Table VIII, the albumin 2S protein differs from the globular 7S and 12S proteins in relative levels of the different amino acids. The key differences arise for Aspartic, Glutamic, Cysteine, Lysine and Proline, although differences are also apparent for most of the amino acids listed. By comparison, the 7S and 12S profiles are almost identical, and would certainly fall within the standard variation for this test. The Glutamic acid quantities also include glutamine, and Aspartic acid includes Asparagine. Both Glutamine and Asparagine are de-aminated during acid hydrolysis, leading to detection of the amino acid analyses.

Table VII includes the molecular weights for the individual amino acids. Combined with the individual quantities, the average molecular weights for the "free" amino acids for 2S, 7S and 12S are shown, and are all just under 135-da. The anhydrous Weight Averaged Molecular Weights are also shown since the proteins are biopolymers of anhydrous amino acids, (each minus a water molecule, excluding one terminal amino acid per polypeptide). In spite of the differences between the two protein types, the average polymeric amino acid molecular weights are almost identical at about 117-da. This means that 2S, with a MALDI-MS determined molecular weight of 14-kDa, consists of approximately 120 amino acids, 7S, with a MALDI-MS molecular weight of 145-kDa, would contain approximately 1,240 amino acids, and 12S would contain double this number, or 2,480 amino acids. Each 7S/12S subunit would contain about 413 amino acids.

Table VIII also indicates the essential amino acids, which cannot be synthesized by humans. The overall content of the eleven essential amino acids is very similar for the two types of protein. The weaknesses in one amino acid are balanced by strengths in other essential amino acids. Lysine is found in 2S at about twice the levels in 7S and 12S. However, the globular proteins have higher overall levels in the aromatic essential amino acids Tyrosine and Phenylalanine, and are generally higher in the aliphatic hydrophobic essential amino acids, with the exceptions of Methionine and Cysteine.

The hydrophobicity of the amino acids in Table VIII is determined according to Gibb's Free Energy values, expressed as KJ per 100 grams amino acid. The Gibb's Free Energy values are listed in *Food Chemistry*, 3rd ed., edited by Owen Fennema, Marcel Dekker, New York, 1996, p 330. The two types of protein do not differ substantially in either weight sums or energy sums for hydrophobicity, but hydrophobicity is also dependent upon the structural orientation of the polypeptides and not just the chemistry of the individual amino acids. Overall, the globular proteins have an Isoelectric Point near neutral pH (7.2) while 2S has an Isoelectric Point above ply 9.0 according to the review of rapeseed proteins by Mieth et al. (Table IX below). 2S is very small in molecular weight, while 7S and 12S are considerably larger with more potentially hydrophobic interior regions that would resist water hydration.

The amino acid composition can be converted into amino acid residues by using an estimate of the number of amino acid residues in the biopolymer. As previously discussed, 2S contains approximately 120 amino acid residues, while 7S contains about 1,240 and 12S about 2,480 residues, based on MALDI-MS analyses.

The following Table IX converts the amino acid analyses results presented above to amino acids for 2S and compares the results with published amino acid residue ranges.

TABLE IX

Comparison of 2S Amino Acid Residues with Literature Values
Values Based on amino acid residues:

| Amino Acid | AL021-I30-02A 2S | 2S @ 120 aa: | 2S Liter. Range[1]: | 2S Liter. Range[2]: |
|---|---|---|---|---|
| Aspartic* | 3.4 | 4 | 2-5 | 2 |
| Threonine[e] | 3.2 | 4 | 3-4 | 4 |
| Serine | 5.2 | 6 | 4-7 | 6-7 |
| Tryptophan[e] | 0.8 | 1 | 1-2 | 1 |
| Glutamic* | 24.6 | 29 | 27-32 | 29-34 |
| Glycine | 7.4 | 9 | 6-10 | 7-9 |
| Alanine | 5.9 | 7 | 6-7 | 6-8 |
| Cystine[e] | 4.9 | 6 | 8 | 7-8 |
| Valine[e] | 4.9 | 6 | 5-7 | 6-7 |
| Methionine[e] | 2.4 | 3 | 1-3 | 2-3 |
| Isoleucine[e] | 3.2 | 4 | 4-7 | 4 |
| Leucine[e] | 6.7 | 8 | 7-9 | 8-9 |
| Tyrosine | 0.9 | 1 | 1-2 | 1 |
| Phenylalanine[e] | 2.1 | 3 | 3-5 | 2-3 |
| Histidine[e] | 2.4 | 3 | 3-4 | 3-4 |
| Lysine[e] | 5.8 | 7 | 5-9 | 6-9 |
| Arginine[e] | 4.9 | 6 | 5-8 | 4-6 |
| Proline | 11.2 | 13 | 13-14 | 12-15 |
| Sum: | 100.0 | 120 | 114-126 | 110-133 |

[e]= 11 essential amino acids
aa= amino acids
MALDI-MS data indicate 2S has MW of about 14,000-da, or 120 polymeric amino acids
*Glutamic acid and aspartic acid are mostly amidated.
[1]Monsalve et al., J. Experimental Botany, Vol. 41, No. 222, pp. 89-94, January 1990.
[2]Mieth et al., Die Nahrung 27, 7, 1983, pp. 675-697.

The conversions agree very well with the published results. The more recent works by Monsalve et al. (1990, per Table IX), plus work by Gehrig et al., Proc. Natl. Acad. Sci. USA, Vol. 93, pp. 3647-3652, April, 1996, and by Ericson et al., J. Biological Chem., Vol. 261, No. 31, pp. 14576-14581, November 1986 give detailed information about 2S and the precursor molecule pro-Napin, including actual amino acid sequencing.

The individual amino acids lie within the ranges from published papers indicated on Table IX. The listed ranges are due to variations within rapeseed varieties and may also be due to minor hydrolytic losses in tho experimental work reported.

Although less is published on cruciferin (12S), what is known about the globular canola proteins is in good agreement with our current findings. The amino acid analysis data was converted to amino acid residues in Table X and compared with published ranges for 12S proteins.

TABLE X

Comparison of 7S/12S Amino Acid Residue with Literature Values

| Amino Acid | Burcon AL017-D29-02A 7S | Burcon AL017-D29-02A 12S | 7S @ 1240 aa: | 12S @ 2480 aa: | Literature Review Range of residues 12S[1] |
|---|---|---|---|---|---|
| Aspartic* | 11.09 | 10.73 | 137 | 266 | 235-270 |
| Threonine | 3.57 | 3.97 | 44 | 98 | |
| Serine | 5.47 | 5.53 | 68 | 137 | |
| Tryptophan | 0.88 | 0.93 | 11 | 23 | |
| Glutamic* | 18.72 | 19.12 | 232 | 474 | 434-531 |
| Glycine | 9.22 | 9.13 | 114 | 226 | |
| Alanine | 6.38 | 6.26 | 79 | 155 | |
| Cystine | 1.25 | 1.33 | 16 | 33 | 14-37 |
| Valine | 6.43 | 6.26 | 80 | 155 | |
| Methionine | 1.48 | 1.30 | 18 | 32 | 13-44 |
| Isoleucine | 4.96 | 4.72 | 62 | 117 | |
| Leucine | 8.44 | 8.32 | 105 | 206 | |
| Tyrosine | 1.87 | 1.83 | 23 | 45 | |
| Phenylalanine | 3.86 | 3.66 | 48 | 91 | |
| Histidine | 1.31 | 1.40 | 16 | 35 | 45-47 |
| Lysine | 2.76 | 2.85 | 34 | 71 | 78-96 |
| Arginine | 5.86 | 5.78 | 73 | 143 | 83-143 |
| Proline | 6.44 | 6.90 | 80 | 171 | |
| Sum: | 100.0 | 100.00 | 1240 | 2480 | |

The average (anhydrous) MW for 7S and 12S is calculated to be 116.8 daltons.
MALDI = MS results indicate a MW of 145-kDa for 7S and 290-kDa for 12S protein (Example 4).
Therefore, 7S would consist of approximately 1,240 amino acid residues and 12S would contain double, or approximately 2,480 residues.
[1] Mieth et al., Die Nahrung, 27, 7, 1983, pp. 678-697.

The published information comes from the review of rapeseed proteins by Mieth et al., 1983. This reference lists the range of specific amino acid residues. The data presented herein is generally in line with these ranges as shown.

The authors (Mieth et al.) refer to the 12S molecule contains 6 major subunits, each consisting of two polypeptides with molecular masses of about 18,000-da and 31,000-da. This information is also in line with what the MALDI-MS data presented in Example 4.

Summary of Disclosure

In summary of this disclosure, the present invention provides novel canola protein isolate compositions having a unique profile of 2S, 7S and 12S proteins as well as individual isolated and purified proteins. Modifications are possible within the scope of the invention.

What we claim is:

1. An isolated and purified 7S protein from canola having a molecular weight of about 145 kDa as determined by MALDI-MS and comprised of three subunits, each approximately 413 amino acids, wherein said canola is a canola protein micellar mass formed by diluting a concentrated saline solution of canola protein extracted from canola oil seed meal under mildly acidic conditions.

* * * * *